United States Patent [19]  
Staiger et al.

[11] Patent Number: 4,503,240  
[45] Date of Patent: Mar. 5, 1985

[54] PROCESS FOR PREPARING 8,12-EPOXY-13,14,15,16-TETRANORLABDANE

[75] Inventors: Gerhard Staiger; Antonio Macri, both of Munich, Fed. Rep. of Germany

[73] Assignee: Consortium Für Elektrochemische Industrie GmbH, Munich, Fed. Rep. of Germany

[21] Appl. No.: 517,980

[22] Filed: Jul. 28, 1983

[30] Foreign Application Priority Data

Oct. 28, 1982 [DE] Fed. Rep. of Germany ....... 3240054

[51] Int. Cl.$^3$ ............................................. C07D 307/92
[52] U.S. Cl. ................................. 549/458; 549/299; 562/598; 568/819
[58] Field of Search ......................................... 549/458

[56] References Cited  
U.S. PATENT DOCUMENTS 3,029,255 4/1962 Stoll ..................................... 549/458

OTHER PUBLICATIONS

Sibiertseva et al., Chem. Abstracts, vol. 93, (1980), 114751w.  
Stork et al., J.A.C.S., vol. 77, pp. 5068–5077, (1955).  
Saito et al., Chemistry Letters, (1981), pp. 757–760.  
Olah, Friedel-Crafts and Related Reactions, (1963), vol. I, pp. 201–202, 258, 259, 262 and 263.

Primary Examiner—Henry R. Jiles  
Assistant Examiner—Bernard I. Dentz  
Attorney, Agent, or Firm—Collard, Roe & Galgano

[57] ABSTRACT

Process for the preparation of 8,12-epoxy-13,14,15,16-tetranorlabdane by way of converting farnesyl bromide to farnesyl cyanide, followed by the saponification of the farnesyl cyanide to homofarnesic acid which is then cyclized to norambreinolide in the presence of titanium tetrachloride, converting the norambreinolide with LiAlH$_4$ to 8-hydroxy-13,14,15,16-tetranorlabdane-12-ol, and cyclization of the diol in the presence of POCl$_3$ to 8,12-epoxy-13,14,15,16-tetranorlabdane. The resulting product exhibits an amber scent, used in perfumery.

8 Claims, No Drawings

PROCESS FOR PREPARING 8,12-EPOXY-13,14,15,16-TETRANORLABDANE

The invention relates to a process for preparing 8,12-epoxy-13,14,15,16-tetranorlabdane by the following steps:

(a) converting farnesyl bromide to farnesyl cyanide;

(b) saponifying farnesyl cyanide to homofarnesic acid;

(c) cyclizing homofarnesic acid to norambreinolide in the presence of $SnCl_4$;

(d) converting norambreinolide with lithium aluminum hydride to 8-hydroxy-13,14,15,16-tetranorlabdane-12-ol; and;

(e) cyclizing 8-hydroxy-13,14,15,16-tetranorlabdane-12-ol in the presence of $POCl_3$.

It is known that the stereoisomeric forms or their mixtures, respectively, of 8,12-epoxy-13,14,15,16-tetranorlabdane exhibit an amber odor. Experiments have been made to synthetically prepare this desired amber scent.

One such experiment is reported by R. C. Cambie, et al. in Austral. J. Chem. 24, 582–591 (1971) relating to a partially synthetic method starting from manoyl oxide, though this is not readily accessible. Another synthesis method is described by G. Lucius in *Chem. Ber.* 93, 2663 (1960) leading from nerolidol to norambreinolide, an intermediate product in the total synthesis of 8,12-epoxy-13,14,15,16-tetranorlabdane by cyclization of homofarnesic acid. The yields, however, are quite unsatisfactory.

It is therefore an object of the present invention to provide a synthesis method for preparing 8,12-epoxy-13,14,15,16-tetranorlabdane which affords an increased yield.

It is a more particular object of the invention to improve the synthesis steps which formerly decreased the yield.

It has now been found that the cyclization of homofarnesic acid to norambreinolide can be considerably improved as regards increase in yield, by carrying out the reaction in the presence of tin tetrachloride. Moreover, it was found that the cyclization of 8-hydroxy-13,14,15,16-tetranorlabdane-12-ol to the desired end product can be carried out with good yields in the presence of phosphorusoxichloride and that especially the quality of the scent is not affected, in contrast to the cyclization taking place in the presence of p-toluene sulfonic acid chloride.

The process according to the invention comprises preparing 8,12-epoxy-13,14,15,16-tetranorlabdane by carrying out the following steps:

(a) converting farnesylbromide to farnesylcyanide;

(b) saponifying farnesylcyanide to homofarnesic acid;

(c) cyclizing homofarnesic acid to norambreinolide in the presence of $SnCl_4$;

(d) converting norambreinolide with lithiumaluminum hydride to 8-hydroxy-13,14,15,16-tetranorlabdane-12-ol; and, (e) cyclizing 8-hydroxy-13,14,15,16-tetranorlabdane-12-ol in the presence of $POCl_3$.

The starting compound used, farnesylbromide, is available by reacting, in a known manner, farnesol with bromides, e.g., phosphorus tribromide. Farnesol is a known commercial substance. An alternative basic chemical is nerolidol, which can be converted to farnesylbromide by treatment with phosphorus tribromide.

Farnesylcyanide (4,8,12-trimethyltrideca-3,7,11-trienoic acid nitrile) can be made available in a known manner by treating farnesyl bromide with alkalimetal cyanide solutions. The operation is best carried out by using a 1.5–3 times of molar excess of cyanide. Particularly high yields are obtained in a two-phase reaction mixture by phase-transfer catalytic reaction.

As inert organic solvents, e.g., hydrocarbon halides, such as dichloromethane and chlorobenzene may be used, or hydrocarbons, e.g., benzene, toluene and xylene. Examples for phase-transfer catalysts are tetrabutylammonium bromide or iodide, and benzyl-trimethyl-ammonium chloride. The second phase is a concentrated, aqueous alkalimetal cyanide solution. The reaction temperatures are in general 0°–120° C. and, preferably, 40°–90° C.

Homofarnesic acid (4,8,12-trimethyltrideca-3,7,11-trienoic acid) becomes available in a manner known, per se, by saponification of farnesyl cyanide. The optimal mode of saponification is treatment in alkaline solutions, e.g., alcohol/water/alkalimetalhydroxide solutions, at temperatures from 20°–120° C. The desired homofarnesic acid is subsequently obtained by acidification of the alkaline reaction mixture and extraction of the free acid from the mixture.

The cyclization of homofarnesic acid to the tricyclic lactone norambreinolide is brought about according to the invention in the presence of tin tetrachloride.

The cyclization reaction is best carried out in inert organic solvents, e.g., hydrocarbon halides, such as dichloromethane or in hydrocarbons, such as cyclohexane, at temperatures from −100° to +25° C., especially from −78° to 0° C. The amount of tin tetrachloride according to the invention is at least equimolar, referring to the amount of homofarnesic acid used. Advantageously, an excess amount of 1.5 to 2 moles are used. Finally, the inorganic ingredients of the reaction mixture are separated by addition of water and the desired norambreinolide is isolated from the organic phase.

The conversion of the lactone norambreinolide to the diol 8-hydroxy-13,14,15,16-tetranorlabdane-12-ol occurs in a manner known, per se, with lithiumaluminum hydride in an anhydrous organic phase. The amount of Li-Al hydride is 0.5 to 2 moles per 1 mole of norambreinolide used. The temperatures maintained are 0°–40° C. In most cases, a solution of Li-Al hydride is first measured into a container and norambreinolide is added in an appropriate amount. Suitable solvents are diethyl ether, tetrahydrofuran, dioxan and ethyleneglycoldimethyl ether.

Finally, the inorganic phase is separated with water and moderately alkaline aqueous solution, and the diol 8-hydroxy-13,14,15,16-tetranorlabdane-12-ol is isolated from the organic phase.

For the conversion of the diol 8-hydroxy-13,14,15,16-tetranorlabdane-12-ol, cyclization according to the invention is carried out in the presence of $POCl_3$ in an equimolar or approximately equimolar amount calculated with reference to the diol used. It is advantageous to measure the diol first into a container adding the appropriate amount of $POCl_3$ next. Suitable solvents are organic bases, e.g., pyridine, picoline, or lutidine.

The reaction temperatures are in the range of −10° to +40° C. Thereupon, the solution is alkalized and finally the end product is extracted from the reaction mixture.

According to the invention it is possible to obtain 8,12-epoxy-13,14,15,16-tetranorlabdane, starting from commercial substances such as farnesol or nerolidol, in considerably increased yields. Obtained is a mixture of three diastereomeric forms with a marked amber scent.

In the following, the invention will be more fully described in an example, but it should be understood that this Example is given by way of illustration only, and not of limitation.

EXAMPLES (a) Preparation of 4,8,12-trimethyltrideca-3,7,11-trienoic acid nitrile (Farnesylcyanide)

A two-phase mixture of 625 g (2.18 moles) farnesylbromide, 216 g (3.27 moles) potassium cyanide, 300 ml water and 20 g (0.062 moles) tetrabutylammonium bromide are heated to 60° C. while stirring vigorously. After the start of the exothermic reaction, the temperature was maintained at 80° C. by cooling. After the reaction subsides, stirring is continued for 2 more hours at 60° C. Then, the organic phase is separated, twice extracted with 200 ml water, and finally dried with sodium sulfate. Obtained were 469 g of farnesylcyanide as a colorless liquid, corresponding to 93% of the theoretical amount.

(b) Preparation of 4,8,12-trimethyltrideca-3,7,11-trienoic acid (Homofarnesic acid)

A mixture of 469 g (2.02 moles) farnesyl cyanide, 287 g potassium hydroxide, 2,500 ml ethanol and 340 ml water were heated under reflux. After 5 hours, the ethanol was evaporated and the residue poured into 10 liters of water. The aqueous solution so obtained was twice extracted with 1 liter diethyl ether, the extracts being discarded, and thereafter acidified with 20% sulfuric acid. Then, the free acid was extracted with diethyl ether. The etheric solution was again washed with water and dried with sodium sulfate. After evaporation of the ether, 419 g (83% of the theoretical) of homofarnesic acid were obtained as a yellow oil.

(c) Preparation of Norambreinolide 419 g (1.6 moles) homofarnesic acid were dissolved in 2.5 liters of anhydrous methylene chloride and cooled down to −78° C. To this solution, 524 g (2 moles) $SnCl_4$ were added dropwise. The reaction mixture was maintained for one hour at this temperature and then further treated as follows: the reaction mixture was poured into 3 liters of water, the organic phase was separated and washed with a saturated solution of sodiumhydrogen carbonate, as well as with water. Finally, the organic phase was dried with sodium sulfate and the solvent evaporated. There remained 390 g (91% of the theoretical) of norambreinolide as a light yellow oil, which slowly crystallizes.

(d) Preparation of 8-hydroxy-13,14,15,16-tetranorlabdane-12-ol

To a suspension of 26.5 g (0.7 moles) $LiAlH_4$ in 300 ml anhydrous diethyl ether, a solution of 87 g (0.35 moles) norambreinolide, dissolved in 500 ml diethyl ether, was added dropwise. The reaction temperature was 20° C. Then, hydrolysis took place by addition of 26 ml water. Furthermore, 25 ml 15% sodium hydroxide solution and 75 ml water was added for the preparation of aluminum hydroxide. The precipitate was filtered off, the organic phase separated and dried with sodium sulfate. After the solvent was evaporated, 79.3 g (90% of the theoretical) of 8-hydroxy-13,14,15,16-tetranorlabdane-12-ol were obtained as a colorless oil.

(e) Preparation of 8,12-Epoxy-13,14,15,16-tetranorlabdane

Into a solution of 75 g (0.29 moles) 8-hydroxy-13,14,15,16-tetranorlabdane-12-ol in 500 ml anhydrous pyridine, 45 g (0.29 moles) $POCl_3$ were added dropwise at 0° C., while stirring. Thereafter, 2 more hours stirring was carried out. Finally, the reaction mixture was introduced into 500 ml 2 n sodium hydroxide solution. The obtained dispersion was extracted with diethyl ether and the extract dried with sodium sulfate.

After evaporation of the diethyl ether, there remained 45 g (65% of the theoretical) of 8,12-epoxy-13,14,15,16-tetranorlabdane. The stereoisomeric mixture exhibited a marked amber scent.

While only one example of the present invention has been described, it is obvious that many changes and modifications may be made thereunto without departing from the spirit and scope of the invention.

What is claimed is:

1. A process for preparing 8,12-epoxy-13,14,15,16-tetranorlabdane, comprising the steps of:
    (a) converting farnesyl bromide to farnesyl cyanide;
    (b) saponifying farnesyl cyanide to homofarnesic acid;
    (c) cyclizing homofarnesic acid to norambreinolide in the presence of $SnCl_4$;
    (d) converting norambreinolide with lithium aluminum hydride to 8-hydroxy-13,14,15,16-tetranorlabdane-12-ol; and
    (e) cyclizing 8-hydroxy-13,14,15,16-tetranolabdane-12-ol in the presence of $POCl_3$.

2. The process of claim 1, wherein said step (c) occurs in a temperature range of about −100° to 25° C.

3. The process of claim 1, wherein said step (c) occurs in a temperature range of about −78° to 0° C.

4. The process of claim 1, wherein said step (d) occurs in a temperature range of about 0° to 40° C.

5. The process of claim 1, wherein said step (e) occurs in a temperature range of about −10° to 40° C.

6. The process of claim 1, wherein said step (a) occurs using 1.5 to 3 times of molar excess of alkali metal cyanide.

7. The process of claim 1, wherein said step (b) occurs in alkaline solutions at temperatures from 20° to 120° C.

8. The process of claim 1, wherein said step (c) produces a yield of norambreinolide in excess of 90% of the theoretical yield for said step.

* * * * *